(12) United States Patent
Wenzel et al.

(10) Patent No.: US 8,987,180 B2
(45) Date of Patent: Mar. 24, 2015

(54) WET WIPES INCLUDING SILICONE REACTIVE AMINO CONTAINING DIMETHICONE COPOLYOLS

(71) Applicant: Kimberly-Clark Worldwide, Inc., Neenah, WI (US)

(72) Inventors: Scott W. Wenzel, Neenah, WI (US); Philip E. Kieffer, Winneconne, WI (US); Jessica Rogers, Appleton, WI (US); Anthony O'Lenick, Dacula, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 57 days.

(21) Appl. No.: 13/717,778

(22) Filed: Dec. 18, 2012

(65) Prior Publication Data

US 2014/0171351 A1    Jun. 19, 2014

(51) Int. Cl.
*A61K 8/898* (2006.01)
*A61Q 19/10* (2006.01)

(52) U.S. Cl.
CPC ............ *A61K 8/898* (2013.01); *A61Q 19/10* (2013.01)
USPC ........................................................ 510/157

(58) Field of Classification Search
USPC ........................................................ 510/157
See application file for complete search history.

(56) References Cited

U.S. PATENT DOCUMENTS

| | | | |
|---|---|---|---|
| 4,100,324 A | 7/1978 | Anderson et al. | |
| 4,167,501 A | 9/1979 | Rooks | |
| 5,045,387 A | 9/1991 | Schmalz | |
| 5,284,703 A | 2/1994 | Everhart et al. | |
| 5,350,624 A | 9/1994 | Georger et al. | |
| 5,378,787 A | 1/1995 | Vrckovnik et al. | |
| 6,121,165 A | 9/2000 | Mackey et al. | |
| 6,168,852 B1 | 1/2001 | Smith, III et al. | |
| 6,280,757 B1 | 8/2001 | McAtee et al. | |
| 6,551,603 B1 | 4/2003 | Vinski et al. | |
| 6,814,974 B2 | 11/2004 | Cole et al. | |
| 7,157,389 B2 | 1/2007 | Branham et al. | |
| 7,276,459 B1 | 10/2007 | Lang et al. | |
| 7,597,780 B2 | 10/2009 | Buder et al. | |
| 7,820,149 B2 * | 10/2010 | Cunningham et al. | 424/70.12 |
| 7,838,588 B2 | 11/2010 | Deroo et al. | |
| 8,124,061 B2 | 2/2012 | Lam et al. | |
| 8,168,578 B2 | 5/2012 | Serobian | |
| 2003/0143263 A1 * | 7/2003 | Durden et al. | 424/443 |
| 2004/0009141 A1 | 1/2004 | Koenig et al. | |
| 2004/0204332 A1 * | 10/2004 | Dastbaz et al. | 510/438 |
| 2006/0039956 A1 | 2/2006 | Hensen et al. | |
| 2006/0073110 A1 * | 4/2006 | Modi | 424/70.13 |
| 2006/0120984 A1 | 6/2006 | Decoster et al. | |
| 2006/0171971 A1 | 8/2006 | Marsh et al. | |
| 2006/0247143 A1 | 11/2006 | Gallagher et al. | |
| 2007/0104674 A1 | 5/2007 | Gordon et al. | |
| 2007/0141936 A1 | 6/2007 | Bunyard et al. | |
| 2008/0171683 A1 * | 7/2008 | Johnson et al. | 510/275 |
| 2009/0155325 A1 | 6/2009 | Wenzel et al. | |
| 2009/0263439 A1 | 10/2009 | Casas-Sanchez et al. | |
| 2010/0028392 A1 | 2/2010 | Cawthorne et al. | |
| 2011/0290437 A1 | 12/2011 | Vogel et al. | |
| 2013/0123376 A1 * | 5/2013 | Herzig et al. | 514/788 |
| 2014/0004163 A1 * | 1/2014 | Mundschau et al. | 424/401 |

FOREIGN PATENT DOCUMENTS

| | | |
|---|---|---|
| EP | 0257824 A2 | 2/1988 |
| WO | 0249604 A1 | 6/2002 |
| WO | WO 2009057046 A2 * | 5/2009 |
| WO | WO 2012055582 A2 * | 5/2012 |

OTHER PUBLICATIONS

International Search Report and Written Opinion of PCT/IB2013/060256 mailed Mar. 18, 2014.

* cited by examiner

*Primary Examiner* — Nicole M Buie-Hatcher
*Assistant Examiner* — M. Reza Asdjodi
(74) *Attorney, Agent, or Firm* — Armstrong Teasdale LLP

(57) ABSTRACT

Personal care compositions and cleansing products including a silicone reactive amino containing dimethicone copolyol are disclosed herein. The compositions and products provide an enhanced wiping experience including improved softness and smooth afterfeel. Further, wipe products including the silicone reactive amino containing dimethicone copolyol provide improved drape of the basesheet, as well as provide a smooth wiping experience with the right amount of glide and a non-tacky afterfeel.

21 Claims, 1 Drawing Sheet

WET WIPES INCLUDING SILICONE REACTIVE AMINO CONTAINING DIMETHICONE COPOLYOLS

FIELD OF THE DISCLOSURE

The field of the disclosure relates generally to silicone reactive amino containing dimethicone copolyols for use in wipe products, and particularly, in flushable moist wipes. The wipe products of the present disclosure have improved softness and drape of the basesheet, as well as provide an enhanced wiping experience with the right amount of glide and a non-tacky, soft & smooth afterfeel.

BACKGROUND OF THE DISCLOSURE

Wipe products have been used in the personal care industry for numerous years, and generally comprise a low surfactant, high water base for cleaning bodily fluids or wiping up menses. In recent years, however, consumers have begun demanding more out of personal care products, including wipes. For example, various wipes have come into the market containing components for soothing skin or containing actives for disinfecting surfaces.

Further, flushable moist wipes have increased in popularity to provide easy disposal after use. Ideally, when a disposable product, such as a flushable moist wipe, is intended to be discarded in either sewer or septic systems, the product should "disperse" and thus sufficiently dissolve or disintegrate in water so as to not present problems under conditions typically found in either household or municipal systems. While much headway has been made in addressing this problem, one of the weak links is that conventional flushable moist wipes require a high electrolyte content in the wetting solution to keep the basesheet intact until it is flushed. This electrolyte content can negatively impact the stability of the solutions containing additional ingredients that are commonly used on the basesheet to enhance the feel of the wiping experience.

Accordingly, there is a need in the art to provide wipe products, and particularly flushable moist wipes, with a stable wetting solution including components that are capable of enhancing the wipe experience. Particularly, components that provide a stable wetting solution and a wipe product with improved softness and drape of the basesheet are particularly desirable. Additionally, it would be advantageous if the solutions included components that provide consumers of the wipe products with improved aesthetics, such as a smooth wiping experience having sufficient glide and non-tacky, soft, smooth afterfeel.

BRIEF DESCRIPTION OF THE DISCLOSURE

The present disclosure is directed to compositions, and in particular wetting solutions (also referred to herein as wetting compositions), which have been developed to address the above-described problems and to be compatible for use with wet wipes for improving aesthetics of the wipes.

In one embodiment, the present disclosure is directed to a cleansing product comprising a substrate and a silicone reactive amino containing dimethicone copolyol having the formula:

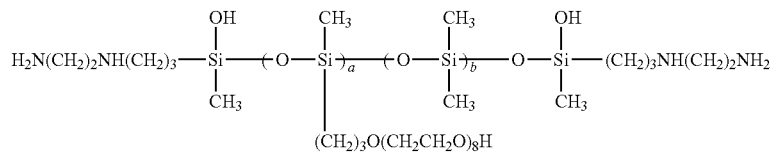

wherein a is an integer ranging from 5 to 500 and b is an integer ranging from 1 to 100.

In another embodiment, the present disclosure is directed to a wet wipe comprising a substrate and a wetting solution comprising a silicone reactive amino containing dimethicone copolyol having the formula:

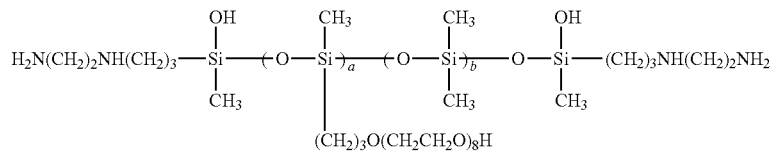

wherein a is an integer ranging from 5 to 500 and b is an integer ranging from 1 to 100. In one particular embodiment, the wet wipe is a flushable moist wipe including a fibrous material having a strength of at least 300 g/in and a dispersibility of no more than 100 g/in.

In yet another embodiment, the present disclosure is directed to a personal care composition for imparting a perceivable aesthetic feel to skin. The composition comprises a carrier and from about 0.01% by weight to about 99.9% by weight of a silicone reactive amino containing dimethicone copolyol having the formula:

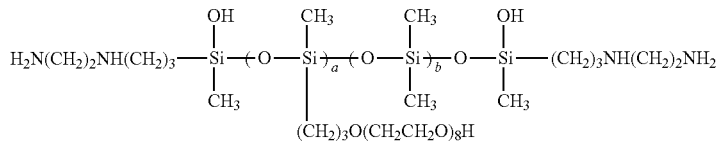

wherein a is an integer ranging from 5 to 500 and b is an integer ranging from 1 to 100.

DETAILED DESCRIPTION OF THE DISCLOSURE

Figure 1A:
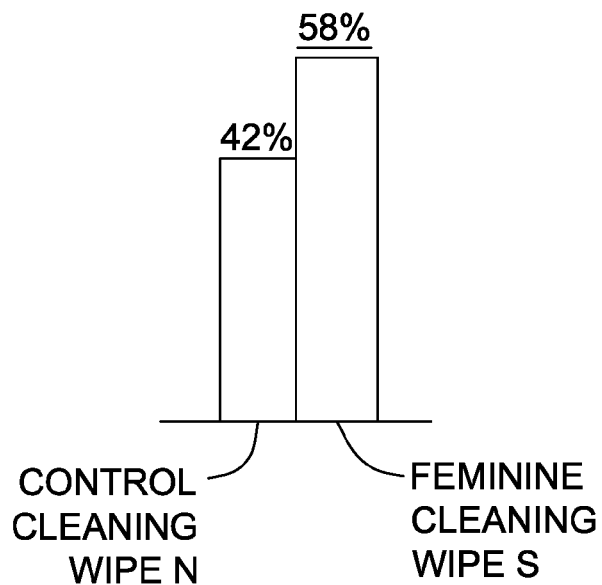
FIG. 1A is a graph comparing overall preference of a feminine cleaning wipe including a silicone amine and a control feminine cleaning wipe as evaluated in Example 3.

The present disclosure is generally directed to stable wetting solutions for use in personal care compositions and wet wipes providing improved aesthetics to the consumer. Particularly, the wetting solutions include a silicone reactive amino containing dimethicone copolyol that allows for a stable solution, even in high electrolyte wetting solutions, while providing a non-tacky, soft, smooth feel to the skin. While described herein for use in the wetting solution of wet wipes and flushable moist wipes, it should be recognized by one skilled in the art that the silicone reactive amino containing dimethicone copolyols used in the products of the present disclosure can be used in other personal care products such as wipes, absorbent articles, bath tissues, cloths, and the like.

The wipe products of the present disclosure include a silicone reactive amino containing dimethicone copolyol of formula

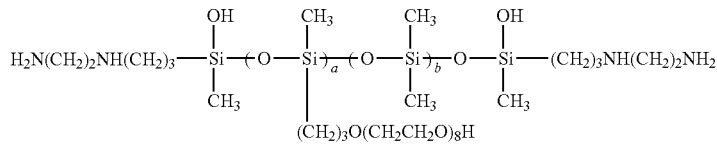

wherein a is an integer ranging from 5 to 500, including from 100 to 450, and including from 180 to 400; and b is an integer ranging from 1 to 100, including from 2 to 10, and including 5. These modified silicones (also referred to herein as silicone amine) provide unique softening, durability and solubility properties when applied to fibrous substrates such as used in the cleansing and personal care products of the present disclosure. The silicone amines provide the products of the present disclosure with improved aesthetics, including improved softness and drape of basesheets, while providing the consumer with an enhanced wiping experience and a soft, smooth afterfeel.

The compounds include (a) an amino group, (b) an alkylene oxide containing portion, (c) a reactive group selected from the group consisting of silanol hydroxyl and alkoxy group. The compounds are self-dispersing in water, by virtue of the alkylene oxide, softening to fiber, by virtue of the amino group and durable by virtue of the silanol and/or hydroxyl group. An additional critically important aspect of the compounds is the fact that they are water soluble or dispersible resulting in stable wetting solutions for use in products such as wet wipes, and in particular, flushable moisture wipes.

The silicone amines are prepared by the sequential reaction of an amino trialkoxy silane and a silanol, followed by the reaction of that product with a dimethicone copolyol in the presence of an alkaline catalyst. An example is as follows:

Reaction Sequence 1

Silanol Containing Silane Preparation

In this step an alkoxy silane is reacted with a silanol to produce an alkoxy silanol, which is a key intermediate in the preparation of the silicone amines used in the products of the present disclosure. The reactants are:

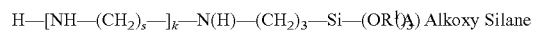

k is an integer ranging from 0 to 3;
s is an integer ranging from 1 to 3;
$R^1$ is methyl or ethyl; and

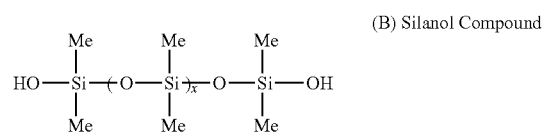

x is an integer typically ranging from 10 to 2000, including an integer ranging from 100 to 800, and including an integer ranging from 200 to 400; and
Me is methyl.

The above reaction results in a polymer, but in the simplest case, the reaction proceeds as follows:

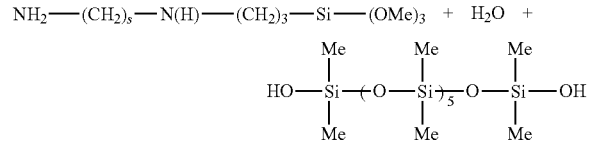

produces:

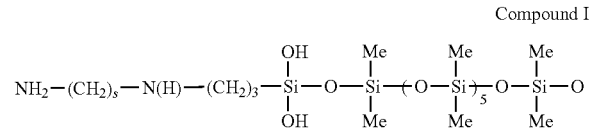

Me is methyl; and
s is an integer ranging from 1 to 3.

The material continues to condense to form the highly branched polymers. This is due to the condensation of the silanol hydroxyl groups.

In order to appreciate the polymeric nature of the structure of Compound I, it is worthwhile to contrast the product with a simple product which results from the condensation of a silane having only a single silanol group in the amino silane. The reaction of:

$$NH_2-(CH_2)_s-N(H)-(CH_2)_3-\underset{\underset{Me}{|}}{\overset{\overset{OMe}{|}}{Si}}-Me$$

mono-methoxy silane with $$HO-\underset{\underset{Me}{|}}{\overset{\overset{Me}{|}}{Si}}-(O-\underset{\underset{Me}{|}}{\overset{\overset{Me}{|}}{Si}})_x-O-\underset{\underset{Me}{|}}{\overset{\overset{Me}{|}}{Si}}-Me$$

mono-silanol Compound produces:

$$NH_2-(CH_2)_s-N(H)-(CH_2)_3-\underset{\underset{Me}{|}}{\overset{\overset{Me}{|}}{Si}}-(O-\underset{\underset{Me}{|}}{\overset{\overset{Me}{|}}{Si}})_x-O-\underset{\underset{Me}{|}}{\overset{\overset{Me}{|}}{Si}}-O-\underset{\underset{Me}{|}}{\overset{\overset{Me}{|}}{Si}}-Me$$

Me is methyl;
x is an integer typically ranging from 10 to 2000, including an integer ranging from 100 to 800, and including an integer ranging from 200 to 400; and
s is an integer ranging from 1 to 3.

The above compound lacks (a) durability due to the lack of an alkoxy or silanol group, (b) water solubility or dispersability due to the lack of an alkylene oxide present in the molecule, and (c) substantivity due to the lack of a three dimensional structure.

The silicone amines used in the products of the present disclosure require that the ratio of silanol hydroxyl equivalents to silane alkoxy group be less than 1:1. This will result in residual alkoxy groups that leads to durability. The functional ratio of silanol groups to alkoxy group generally ranges from about 1:2 to about 1:3.

Particularly suitable reactants include:

$$NH_2-(CH_2)_s-N(H)-(CH_2)_2-Si-(OR^1)_3 \quad\quad \text{Alkoxy Silane}$$

$R^1$ is methyl or ethyl;
s is an integer ranging from 1 to 3; and $$HO-\underset{\underset{Me}{|}}{\overset{\overset{Me}{|}}{Si}}-(O-\underset{\underset{Me}{|}}{\overset{\overset{Me}{|}}{Si}})_x-O-\underset{\underset{Me}{|}}{\overset{\overset{Me}{|}}{Si}}-OH$$

Silanol Compound x is an integer typically ranging from 10 to 2000, including an integer ranging from 100 to 800, and including an integer ranging from 200 to 400; and
Me is methyl.

The resulting polymer network in its most simple form resembles the following:

$$R^2-\underset{\underset{R^3}{|}}{\overset{\overset{R^3}{|}}{Si}}-(O-\underset{\underset{R^3}{|}}{\overset{\overset{R^3}{|}}{Si}})_t-(O-\underset{\underset{Me}{|}}{\overset{\overset{Me}{|}}{Si}})_u-O-\underset{\underset{R^3}{|}}{\overset{\overset{R^3}{|}}{Si}}-R^2$$

wherein:
Me is methyl;
$R^2$ is $-(CH_2)_3-N(H)-((CH_2)_s-NH)_k-H$;
$R^3$ is selected from the group consisting of —OMe and OH;
s is an integer ranging from 1 to 3;
t is an integer ranging from 10 to 2000;
u is an integer ranging from 0 to 2000; and
k is an integer ranging from 0 to 3.

Since the free silanol groups in $R^3$ also react, a complex three dimensional polymer develops. The polymer is surprisingly reproducible and is controlled by the ratio of silane alkoxy group to silanol group. A suitable ratio includes silanol group to alkoxy group of from about 1:2 to about 1:3, and including about 1:2.5.

The compounds so prepared are then reacted with dimethicone copolyols to produce the silicone amine, having improved solubility and dispersibility, even in a wetting solution having high electrolyte content. The silicone amines provide the products with improved aesthetics, such as improved smoothness and afterfeel. For example, wipe products including the silicone amines show improved softness and drape, and further provide the consumer with an enhanced wiping experience, having sufficient glide and a non-tacky, soft & smooth afterfeel.

Dimethicone copolyols are known. They conform to the following structures:

$$R'-\underset{\underset{Me}{|}}{\overset{\overset{Me}{|}}{Si}}-[O-\underset{\underset{Me}{|}}{\overset{\overset{Me}{|}}{Si}}]_o-O-\underset{\underset{Me}{|}}{\overset{\overset{Me}{|}}{Si}}-R'$$

Terminal Dimethicone Copolyols wherein:
Me is methyl;
R' is $-(CH_2)_3-O-(EO)_{a'}-(PO)_{b'}-H$;
o is an integer ranging from 1 to 100, and in a particularly suitable embodiment, o is an integer ranging from 2 to 10, including 5;
EO is $-(CH_2CH_2-O)-$;
PO is $-(CH_2CH(CH_3)-O)-$;
a' and b' are independently integers ranging from 0 to 20. In one embodiment, a' is an integer ranging from 5 to 15, including an integer ranging from 8 to 10, and b' is 0.

$$Me-\underset{\underset{Me}{|}}{\overset{\overset{Me}{|}}{Si}}-[O-\underset{\underset{Me}{|}}{\overset{\overset{Me}{|}}{Si}}]_o-[O-\underset{\underset{R}{|}}{\overset{\overset{Me}{|}}{Si}}]_q-O-\underset{\underset{Me}{|}}{\overset{\overset{Me}{|}}{Si}}-Me$$

Comb Dimethicone Copolyols wherein:
Me is methyl;
o is an integer ranging from 1 to 100, and in a particularly suitable embodiment, o is an integer ranging from 2 to 10, including 5;

q is an integer ranging from 0 to 500, and in a particularly suitable embodiment, q is an integer ranging from 4 to 20;

R is —$(CH_2)_2$—O-$(EO)_{a'}$—$(PO)_{b'}$—H;

EO is —$(CH_2CH_2$—O)—;

PO is —$(CH_2CH(CH_3)$—O)—; and a' and b' are integers independently ranging from 0 to 20. In one embodiment, a' is an integer ranging from 5 to 15, and particularly, an integer ranging from 8 to 10, and b' is 0.

The insertion reaction results in the placing of the dimethicone copolyol compound within the above mentioned highly branched silicone compound. The dimethicone copolyol is added at a weight percent of from about 50% to about 98%.

As noted above, the silicone amines may be incorporated into personal care products and wipe products to improve the perceivable aesthetics of these products. In one particular aspect, the present disclosure is directed to wet wipes. As used herein, the term "wet wipe" means a wipe that includes greater than about 70% (by weight substrate) moisture content. Specifically, suitable wipes of the present disclosure can include wet wipes, hand wipes, face wipes, cosmetic wipes, household wipes, industrial wipes, and the like.

Materials suitable for the substrate of the wipes are well known to those skilled in the art, and are typically made from a fibrous sheet material which may be either woven or non-woven. For example, suitable materials for use in the wipes may include nonwoven fibrous sheet materials which include meltblown, coform, air-laid, bonded-carded web materials, hydroentangled materials, and combinations thereof. Such materials can be comprised of synthetic or natural fibers, or a combination thereof. Typically, the wipes of the present disclosure define a basis weight of from about 25 grams per square meter to about 120 grams per square meter, including from about 40 grams per square meter to about 90 grams per square meter.

In one particular embodiment, the wipes of the present disclosure comprise a coform basesheet of polymer fibers and absorbent fibers having a basis weight of from about 45 to about 80 grams per square meter, including about grams per square meter. Such coform basesheets are manufactured generally as described in U.S. Pat. No. 4,100,324, issued to Anderson, et al. (Jul. 11, 1978); U.S. Pat. No. 5,284,703, issued to Everhart, et al. (Feb. 8, 1994); and U.S. Pat. No. 5,350,624, issued to Georger, et al. (Sep. 27, 1994), which are incorporated by reference to the extent to which they are consistent herewith.

Typically, such coform basesheets include a gas-formed matrix of thermoplastic polymeric meltblown fibers and cellulosic fibers. Various suitable materials may be used to provide the polymeric meltblown fibers, such as, for example, polypropylene microfibers. Alternatively, the polymeric meltblown fibers may be elastomeric polymer fibers, such as those provided by a polymer resin. For instance, Vistamaxx® elastic olefin copolymer resin, designated PLTD-1810 and available from ExxonMobil Corporation (Houston, Tex.), or KRATON G-2755, available from Kraton Polymers (Houston, Tex.), may be used to provide stretchable polymeric meltblown fibers for the coform basesheets. Other suitable polymeric materials or combinations thereof may alternatively be utilized as known in the art.

The coform basesheet additionally may include various absorbent cellulosic fibers, such as, for example, wood pulp fibers. Suitable commercially available cellulosic fibers for use in the coform basesheets can include, for example, NF 405, which is a chemically treated bleached southern softwood Kraft pulp, available from Weyerhaeuser Co. of Federal Way (Wash.); NB 416, which is a bleached southern softwood Kraft pulp, available from Weyerhaeuser Co.; CR-0056, which is a fully debonded softwood pulp, available from Bowater, Inc. (Greenville, S.C.); Golden Isles 4822 debonded softwood pulp, available from Koch Cellulose (Brunswick, Ga.); and SULPHATATE HJ, which is a chemically modified hardwood pulp, available from Rayonier, Inc. (Jesup, Ga.).

The relative percentages of the polymeric meltblown fibers and cellulosic fibers in the coform basesheet can vary over a wide range depending upon the desired characteristics of the wipes. For example, the coform basesheet may comprise from about 10 weight percent to about 90 weight percent, including from about 20 weight percent to about 60 weight percent, and including from about 25 weight percent to about 35 weight percent of the polymeric meltblown fibers based on the dry weight of the coform basesheet being used to provide the wipes.

In another embodiment, the wipe substrate may be an airlaid nonwoven fabric. The basis weights for airlaid nonwoven fabrics may range from about 20 to about 200 grams per square meter (gsm) with staple fibers having a denier of about 0.5-10 and a length of about 6-15 millimeters. Wet wipes may generally have a fiber density of about 0.025 g/cc to about 0.2 g/cc. Wet wipes may generally have a basis weight of about 20 gsm to about 150 gsm, including from about 30 to about 90 gsm, and including from about 50 gsm to about 75 gsm. Processes for producing airlaid non-woven basesheets are described in, for example, published U.S. Pat. App. No. 200610008621, herein incorporated by reference to the extent it is consistent herewith.

In an alternative embodiment, the wipes of the present disclosure can comprise a composite which includes multiple layers of materials. For example, the wipes may include a three layer composite which includes an elastomeric film or meltblown layer between two coform layers as described above. In such a configuration, the coform layers may define a basis weight of from about 15 grams per square meter to about 30 grams per square meter and the elastomeric layer may include a film material such as a polyethylene metallocene film. Such composites are manufactured generally as described in U.S. Pat. No. 6,946,413, issued to Lange, et al. (Sep. 20, 2005), which is hereby incorporated by reference to the extent it is consistent herewith.

In another embodiment, the silicone amine compounds can be used in flushable moist wipes for easy disposable and biodegradability. The flushable moist wipes typically include the fibrous sheet materials as discussed above for wet wipes, and further include a binder composition including a triggerable polymer for maintaining wet strength under controlled conditions, while dissolving or dispersing in a reasonable period of time in soft or hard water, such as found in toilets and sinks around the world. Suitable binder compositions for use in the flushable moist wipes of the present disclosure are known in the art and include, for example, binder compositions described in published U.S. Pat. App. Nos. 20070141936 and 20110290437 and U.S. Pat. No. 7,157,389, which are hereby incorporated by reference to the extent they are consistent herewith.

The binder compositions used in the flushable moist wipes of the present disclosure function as adhesives for tissue, airlaid pulp, and other nonwoven webs and provide sufficient in-use strength (typically ≥250 g/in.) in salt solutions, especially sodium chloride. Moreover, the flushable moist wipes of the present disclosure possess an in-use wet tensile strength of at least 100 g/in when soaked with 10% to 400% by weight wetting solution containing more than 0.5% by weight monovalent and/or divalent salts, such as NaCl, $ZnCl_2$ and/or $CaCl_2$ or mixtures thereof, and a tensile strength of less than about 30 g/in after being soaked in soft water or hard water containing up to 200 ppm concentration of $Ca^{2+}$ and/or $Mg^{2+}$ for 24 hours or less, preferably after about one hour.

Such wipes can have cross-direction wet tensile ("CDWT") values of 250 g/in or greater, and after soaking values (also referred to herein as dispersibility) of no more than 100 g/in, more specifically about 80 g/in or less, and most specifically about 50 g/in or less.

As mentioned above, particularly suitable products for use in combination with the silicone amine compounds is a wet wipe or flushable moist wipe. In addition to the wipe substrate, these wipe products also comprise a wetting solution. The wetting solution can be any liquid, which can be absorbed into the wipe basesheet and may include any suitable components, which provide the desired wiping properties.

In one embodiment, the wetting composition includes one or electrolytes. Electrolytes for use in wet wipes and flushable moist wipes are well known in the art and are described more fully in U.S. Pat. No. 7,157,389 and U.S. Pat. App. No. 20110290437, which are incorporated herein by reference to the extent they are consistent herewith. Suitable examples include salts having both monovalent and multivalent ions, such as sodium chloride, sodium bromide, potassium chloride, ammonium chloride, ammonium sulfate, zinc chloride, calcium chloride, magnesium chloride, magnesium sulfate, sodium nitrate, sodium methyl sulfate, and combinations thereof. The electrolytes are typically included in amounts ranging from 0.3% by weight to about 10% by weight, including from about 0.5% by weight to about 5% by weight, including about 1% by weight to about 4% by weight, and including about 1% by weight to about 2% by weight.

In one embodiment, the wetting solutions may further include surfactants. Examples of suitable surfactants include, for example, anionic surfactants, cationic surfactants, amphoteric surfactants, zwitterionic surfactants, nonionic surfactants, and combinations thereof. Specific examples of suitable surfactants are known in the art and include those suitable for incorporation into personal care compositions and wipe products. The wetting solutions may suitably include one or more surfactant in an amount of from about 0.01% by weight to about 80% by weight surfactant, including from about 0.01% by weight to about 60% by weight, including from about 0.01% by weight to about 40% by weight, including from about 0.01% by weight to about 20% by weight, and including from about 0.01% by weight to about 10% by weight.

Other exemplary components in the wetting solutions may include water, emollients, surfactants, fragrances, preservatives, organic or inorganic acids, chelating agents, pH buffers, or combinations thereof as are well known to those skilled in the art. Exemplary components include, for example, those described in published U.S. Pat. App. No. 20070141936, which is hereby incorporated by reference to the extent it is consistent herewith. Further, the wetting solution may also contain lotions, medicaments, and/or antimicrobials.

The wetting solution may suitably be incorporated into the wipe in an add-on amount of from about 10% (by weight of the treated substrate) to about 600% (by weight of the treated substrate), including from about 50% (by weight of the treated substrate) to about 500% (by weight of the treated substrate), including from about 100% (by weight of the treated substrate) to about 400% (by weight of the treated substrate), and including from about 200% (by weight of the treated substrate) to about 300% (by weight of the treated substrate).

The desired wetting solution add-on amounts may vary depending on the composition of the wipe substrate. Typically, however, for coform basesheets, the composition add-on amount will be from about 250% (by weight of the treated substrate) to about 350% (by weight of the treated substrate), and more typically about 330% (by weight of the treated substrate). For air-laid basesheets, the composition add-on amount will typically be from about 200% (by weight of the treated substrate) to about 300% (by weight of the treated substrate), and more typically will be about 235% (by weight of the treated substrate).

These add-on amounts will preferably result in a wipe product comprising the silicone amine compound in an add-on amount of from about 0.05% (by weight of treated substrate) to about 50% (by weight of treated substrate), including from about 0.1% (by weight of the treated substrate) to about 25% (by weight of the treated substrate). The add-on amount of silicone amine compound will depend on the concentration of the silicone amine compound in the wetting solution and the total add-on amount of the solution to the wipe product.

Alternatively, the silicone amine compound may be formulated with one or more conventional pharmaceutically-acceptable and compatible carrier materials to form a personal care composition having improved stability, afterfeel and smoothness. The composition may take a variety of forms including, without limitation, aqueous solutions, gels, balms, lotions, suspensions, creams, milks, salves, ointments, sprays, foams, solid sticks, aerosols, and the like. Carrier materials suitable for use with the silicone amine compound include those well-known for use in the cosmetic and medical arts as a basis for ointments, lotions, creams, salves, films, aerosols, gels, suspensions, sprays, foams, and the like, and may be used in their art-established levels.

Non-limiting examples of suitable carrier materials include water; glycols such as propylene glycol, butylene glycol, and ethoxydiglycol; lower chain alcohols such as ethanol and isopropanol; glycerin and glycerin derivatives; natural oils such as jojoba oil and sunflower oil; synthetic oils such as mineral oil; silicone derivatives such as cyclomethicone, and other pharmaceutically acceptable carrier materials. As will be recognized by one skilled in the art, the relative amounts of carrier material and other components that can be used to formulate the composition will be dictated by the nature of the composition. The levels can be determined by routine experimentation in view of the disclosure provided herein.

In one embodiment, the compositions may include water. The compositions can suitably include water in an amount of from about 0.1% (by weight of the composition) to about 99% (by weight of the composition), more typically, from about 40% (by weight of the composition) to about 99% (by weight of the composition), and more typically, from about 60% (by weight of the composition) to about 99% (by weight of the composition).

The compositions may include the silicone amine compound in an amount of from about 0.1% (by weight of the composition) to about 99.9% (by weight of the composition), more typically, from about 0.05% (by weight of the composition) to about 50% (by weight of the composition), and more typically, from about 0.01% (by weight of the composition) to about 25% (by weight of the composition).

Similar to the wetting compositions described above, the personal care compositions may further include additional agents that impart a beneficial effect on skin and/or further act to improve the aesthetic feel of the compositions described herein. Examples of suitable skin benefit ingredients include emollients, sterols or sterol derivatives, natural and synthetic fats or oils, viscosity enhancers, rheology modifiers, polyols, surfactants, alcohols, esters, silicones, clays, starch, cellulose, particulates, moisturizers, film formers, slip modifiers, surface modifiers, skin protectants, humectants, sunscreens, and the like. Exemplary additional agents are known in the art, and include, for example, those described in U.S. Pat. No. 7,820,149, issued to Cunningham et al., and incorporated herein by reference to the extent that it is consistent herewith.

EXAMPLES

The following non-limiting Examples are provided to further illustrate the present disclosure.

Example 1

In this Example, various silicone containing compounds were incorporated into a wetting solution and analyzed visually for solubility in the solution.

The wetting solution included: 2% by weight sodium chloride; 0.45% by weight sodium benzoate; 0.17% by weight malic acid; and 97.38% by weight water. To the wetting solution, various amounts of a silicone containing compound, as set forth in the table below, were added in order to reach 100% w/w. Visual evaluations of the solutions including the silicone-containing compounds were conducted after the solutions were left for 24 hours at room temperature. Solutions 5, 6, and 8 hazed and precipitate formed. Solutions 1, 2, 3, 4, 7, 9, 10, 11, and 12 formed a clear, homogenous solution.

| Solution | Generic Chemical Name | Trade Name/Commercial Name | Commercial Supplier | Amount Added to Solution (Wt %) | % Active | Total Active Amount Added to Solution (wt %) |
|---|---|---|---|---|---|---|
| 1 | Silicone anionic cationic complex | Softener Example #1 | Siltech Corporation (Toronto, Canada) | 1.0 | 100 | 1.0 |
| 1 | Silicon anionic cationic complex | Softener Example #1 | Siltech Corporation (Toronto, Canada) | 2.0 | 100 | 2.0 |
| 2 | Silicone anionic cationic complex | Softener Example #2 | Siltech Corporation (Toronto, Canada) | 1.0 | 100 | 1.0 |
| 2 | Silicon anionic cationic complex | Softener Example #2 | Siltech Corporation (Toronto, Canada) | 2.0 | 100 | 2.0 |
| 3 | Silicone anionic cationic complex | Softener Example #3 | Siltech Corporation (Toronto, Canada) | 1.0 | 30 | 0.3 |
| 3 | Silicone anionic cationic complex | Softener Example #3 | Siltech Corporation (Toronto, Canada) | 3.33 | 30 | 0.999 |
| 3 | Silicone anionic cationic complex | Softener Example #3 | Siltech Corporation (Toronto, Canada) | 6.7 | 30 | 2.01 |
| 4 | Silicone anionic cationic complex | Softener Example #4 | Siltech Corporation (Toronto, Canada) | 1.0 | 30 | 0.3 |
| 4 | Silicone anionic cationic complex | Softener Example #4 | Siltech Corporation (Toronto, Canada) | 3.3 | 30 | 0.99 |
| 4 | Silicone anionic cationic complex | Softener Example #4 | Siltech Corporation (Toronto, Canada) | 6.7 | 30 | 2.01 |
| 5 | Silicone quat | Softener Example #5 | Siltech Corporation (Toronto, Canada) | 1.0 | 50 | 0.5 |
| 6 | Silicone quat | Softener Example #6 | Siltech Corporation (Toronto, Canada) | 1.0 | 50 | 0.5 |

-continued

| Solution | Generic Chemical Name | Trade Name/Commercial Name | Commercial Supplier | Amount Added to Solution (Wt %) | % Active | Total Active Amount Added to Solution (wt %) |
|---|---|---|---|---|---|---|
| 7 | silicone amine | $H_2N(CH_2)_2NH(CH_2)_3$—Si(OH)(CH$_3$)—(O—Si(CH$_3$)((CH$_2$)$_3$O(CH$_2$CH$_2$O)$_8$H))$_{180}$—(O—Si(CH$_3$)$_2$)$_5$—O—Si(OH)(CH$_3$)—(CH$_2$)$_3$NH(CH$_2$)$_2$NH$_2$  Silamine® C-100 | Siltech Corporation (Toronto, Canada) | 1.0 | 50 | 0.5 |
| 7 | silicone amine | Silamine® C-100 | Siltech Corporation (Toronto, Canada) | 3.3 | 50 | 1.65 |
| 7 | silicone amine | Silamine® C-100 | Siltech Corporation (Toronto, Canada) | 6.7 | 50 | 3.35 |
| 7 | silicone amine | Silamine® C-100 | Siltech Corporation (Toronto, Canada) | 2.0 | 50 | 1.0 |
| 7 | silicone amine | Silamine® C-100 | Siltech Corporation (Toronto, Canada) | 4.0 | 50 | 2.0 |

-continued

| Solution | Generic Chemical Name | Trade Name/Commercial Name | Commercial Supplier | Amount Added to Solution (Wt %) | % Active | Total Active Amount Added to Solution (wt %) |
|---|---|---|---|---|---|---|
| 7 | silicone amine | H$_2$N(CH$_2$)$_2$NH(CH$_2$)$_3$—Si(OH)(CH$_3$)—(O—Si(CH$_3$)((CH$_2$)$_3$O(CH$_2$CH$_2$O)$_8$H))$_{180}$—(O—Si(CH$_3$)$_2$)$_5$—O—Si(OH)(CH$_3$)—(CH$_2$)$_3$NH(CH$_2$)$_2$NH$_2$<br>Silamine® C-100 | Siltech Corporation (Toronto, Canada) | 6.0 | 50 | 3.0 |
| 8 | Non-silicone phospholipid | Softener Example #8 | Siltech Corporation (Toronto, Canada) | 1.0 | 30 | 0.3 |
| 9 | silicone quat | Softener Example #9 | Siltech Corporation (Toronto, Canada) | 1.0 | 70 | 0.7 |
| 10 | silicone amine | H$_2$N(CH$_2$)$_2$NH(CH$_2$)$_3$—Si(OH)(CH$_3$)—(O—Si(CH$_3$)((CH$_2$)$_3$O(CH$_2$CH$_2$O)$_8$H))$_{200}$—(O—Si(CH$_3$)$_2$)$_5$—O—Si(OH)(CH$_3$)—(CH$_2$)$_3$NH(CH$_2$)$_2$NH$_2$<br>Silamine® PD | Siltech Corporation (Toronto, Canada) | 1.0 | 90 | 0.9 |
| 10 | silicone amine | H$_2$N(CH$_2$)$_2$NH(CH$_2$)$_3$—Si(OH)(CH$_3$)—(O—Si(CH$_3$)((CH$_2$)$_3$O(CH$_2$CH$_2$O)$_8$H))$_{200}$—(O—Si(CH$_3$)$_2$)$_5$—O—Si(OH)(CH$_3$)—(CH$_2$)$_3$NH(CH$_2$)$_2$NH$_2$<br>Silamine® PD | Siltech Corporation (Toronto, Canada) | 1.11 | 90 | 0.999 |
| 10 | silicone amine | H$_2$N(CH$_2$)$_2$NH(CH$_2$)$_3$—Si(OH)(CH$_3$)—(O—Si(CH$_3$)((CH$_2$)$_3$O(CH$_2$CH$_2$O)$_8$H))$_{200}$—(O—Si(CH$_3$)$_2$)$_5$—O—Si(OH)(CH$_3$)—(CH$_2$)$_3$NH(CH$_2$)$_2$NH$_2$<br>Silamine® PD | Siltech Corporation (Toronto, Canada) | 2.22 | 90 | 1.998 |

-continued

| Solution | Generic Chemical Name | Trade Name/Commercial Name | Commercial Supplier | Amount Added to Solution (Wt %) | % Active | Total Active Amount Added to Solution (wt %) |
|---|---|---|---|---|---|---|
| 10 | silicone amine | $H_2N(CH_2)_2NH(CH_2)_3-Si(CH_3)(OH)-(O-Si(CH_3)_2)_{200}-(O-Si(CH_3)((CH_2)_3O(CH_2CH_2O)_8H))_5-O-Si(CH_3)(OH)-(CH_2)_3NH(CH_2)_2NH_2$ | Siltech Corporation (Toronto, Canada) | 3.33 | 90 | 2.997 |
| 11 | Salt of Silamine® PD | Softener Example #11 | Siltech Corporation (Toronto, Canada) | 1.0 | 75 | 0.75 |
| 12 | Salt of Silamine® PD | Softener Example #12 | Siltech Corporation (Toronto, Canada) | 1.0 | 90 | 0.9 |

Example 2

In this Example, silicone-containing compounds of solutions 1, 2, 3, 4, 7, 9, 10, 11, and 12 of Example 1 were added to a basesheet, and the basesheets including the silicone-containing compounds were evaluated for aesthetic feel during use.

Basesheets made of airlaid material and having a basis weight of approximately 73 gsm were coated with a 235% add-on amount of the solutions. The basesheets were evaluated for how the sheets felt upon wiping on the skin, how the solution felt while drying after wiping (i.e., dry down), and how the skin felt once dry. Each basesheet including the solution was independently rubbed once on the volar of a tester's forearm. Results are shown in the table below.

| Solution | Amount Added to Solution (Wt %) | % Active | Total Active Amount Added to Solution (wt %) | Observations |
|---|---|---|---|---|
| 1 | 1.0 | 100 | 1.0 | Smooth application, very draggy drydown |
| 1 | 2.0 | 100 | 2.0 | Nice wet feel, draggy drydown, no sheet to sheet adhesion |
| 2 | 1.0 | 100 | 1.0 | Ok wiping, draggy drydown |
| 2 | 2.0 | 100 | 2.0 | Ok wet, draggy drydown, tacky, no sheet to sheet adhesion |
| 3 | 1.0 | 30 | 0.3 | Feels wet, draggy drydown, tacky |
| 3 | 3.33 | 30 | 0.999 | Ok wet, draggy drydown, tacky |
| 3 | 6.7 | 30 | 2.01 | Nice glide, draggy drydown |
| 4 | 1.0 | 30 | 0.3 | Noisy wiping, tacky drydown |
| 4 | 3.3 | 30 | 0.99 | Nice wet, tacky drydown |
| 4 | 6.7 | 30 | 2.01 | Good glide, sticky drydown |
| 7 | 1.0 | 50 | 0.5 | Lightly substantive, draggy drydown |
| 7 | 3.3 | 50 | 1.65 | Ok wiping, draggy drydown |
| 7 | 6.7 | 50 | 3.35 | Good glide, slightly tacky drydown |
| 7 | 2.0 | 50 | 1.0 | Ok wipe, tacky drydown |
| 7 | 4.0 | 50 | 2.0 | Nice feeling basesheet, slight tack |
| 7 | 6.0 | 50 | 3.0 | Good glide, tacky drydown |
| 9 | 1.0 | 70 | 0.7 | Needs a bit more glide, some drag |
| 10 | 1.11 | 90 | 0.999 | Good glide, no tack |
| 10 | 2.22 | 90 | 1.998 | Good glide, no tack, powdery slip |
| 10 | 3.33 | 90 | 2.997 | Lotion wet, tacky drydown, nice afterfeel |
| 11 | 1.0 | 75 | 0.75 | Nice glide, slightly tacky, good afterfeel |
| 12 | 1.0 | 90 | 0.9 | Ok basesheet, draggy drydown |

As shown in the table, basesheets including solutions 7 and 10 provided increased hand feel, increased glide on the skin while wiping, and provided an enhanced feel upon dry down. Solutions 7 and 10 were fairly high in silicone content so these results were unexpected for multiple reasons. As silicone is very hydrophobic and, typically, is insoluble in water, it would have been expected that these solutions would be insoluble in the highly aqueous wetting solutions, and should not have formed homogenous solutions. Additionally, solutions 7 and 10 containing Silamine® chemistries with high silicone content should not have been able to wet out the basesheet without beading up on the surface of the basesheet.

As this was unexpected, an investigation of Silamine® PW13065 was included to further understand whether additional silicone on the molecule would garner an even more improved aesthetic soft feel. Particularly, Silamine® C-100 (solution 7) has a lower amount of silicone than Silmine® PD (solution 10), and Silamine® PD has a lower amount of silicone than Silamine® PW13065.

Solutions including Silamine® PW13065, having the formula

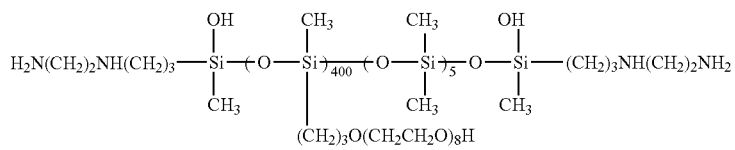

and available from Siltech Corporation, Toronto, Canada, were evaluated for solubility in a wetting solution consisting of materials described in Example 1. Surprisingly and unexpectedly, the Silamine® PW13065, having the highest silicone content, was indeed soluble and homogenous in highly aqueous wetting solutions.

Further, solutions containing Silamine® PW13065 were prepared and coated with 235% add-on amount of solution to basesheets made of airlaid material and having a basis weight of approximately 73 gsm. Again, surprisingly, the solutions containing Silamine® PW13065 were able to wet out the basesheet without beading up on the surface of the basesheet. The basesheets were evaluated for how the sheets felt upon wiping on the skin, how the solution felt while drying after wiping (i.e., dry down), and how the skin felt once dry. Each basesheet including the solution was independently rubbed once on the volar of a tester's forearm. Results are shown in the table below.

| Softener # | Wt % | % Active | Total % Softener | Observations |
|---|---|---|---|---|
| PW13065 | 0.5 | 90 | 0.45 | Microfiber feel to wipe, nice glide, no tack |
| PW13065 | 1.0 | 90 | 0.9 | Basesheet feels awesome, velvety, no tack |
| PW13065 | 5.0 | 90 | 4.5 | Good basesheet, nice glide, no tack |

As can be seen from the results above, the Silamine® PW13065 solutions provided evaluators of the wipe product with improved aesthetics, such as improved feel of the wipe in hand, increased glide and a non-tacky, soft, smooth afterfeel.

Example 3

In this Example, a feminine cleaning wipe including a wetting composition including Silamine® PW13065 was prepared and evaluated for enhanced aesthetics and smooth feel on the skin of consumers. The aesthetics of this feminine wipe were compared to a control code without Silamine® PW13065 and two commercial feminine cleaning wipes without Silamine® PW13065.

Test feminine wipe S had the following wetting composition:

| INCI Name | Weight % |
|---|---|
| Water | Q.S. |
| Silamine ® PW13065 | 0.5 |
| Sodium Chloride | 2.0 |
| Saccharomyces Ferment | 2.0 |
| Polysorbate 20 | 0.7 |
| Fragrance | 0.2 |

-continued

| INCI Name | Weight % |
|---|---|
| 1,2-Hexanediol, Caprylyl Glycol | 1.0 |
| Malic Acid | As Needed |
| Total | 100.00 |

The test wetting composition was prepared by mixing water and Silamine® PW13065. Polysorbate-20 and fragrance were mixed in a separate vessel until uniform. Once uniform, this mixture was added to the water and Silamine® PW13065 mixture. 1,2-hexaneodiol, caprylyl glycol was added and then sodium chloride was added to the mixture. The pH of the wetting composition was adjusted to 3.0 with malic acid. The wetting composition was applied to the test feminine wipe S at an add-on amount of approximately 235% add-on. The control cleaning wipes tested were control wipe N (available from Kimberly-Clark, Neenah, Wis.); commercial control wipe A (available from Procter & Gamble, Cincinnati, Ohio); and commercial control wipe E (available from Fleet Laboratories, Lynchburg, Va.). The test wipe, control wipe, and commercial control wipes were evaluated for overall preference, including attributes such as smoothness, clean feel, long-lasting clean feel, and fresh feel.

Female test subjects, aged 40-65 and who were current users of feminine cleaning wipes or experienced vaginal odor in the past three months, were randomly provided with two plastic bags (each bag containing one of the four compared wipes), each bag including seven wipes for use over a period of 7 days. One bag was labeled "use first", and a second bag was labeled "use second". The number of subjects tested for each comparison is as follows: wipe S v. wipe N (189); wipe S v. wipe A (185); and wipe S v. wipe E (188). The subjects then provided post-use evaluations of comparing their two wipes relating to the above skin feel attributes. The results are shown in FIGS. 1A-1B.

Figure 1B:
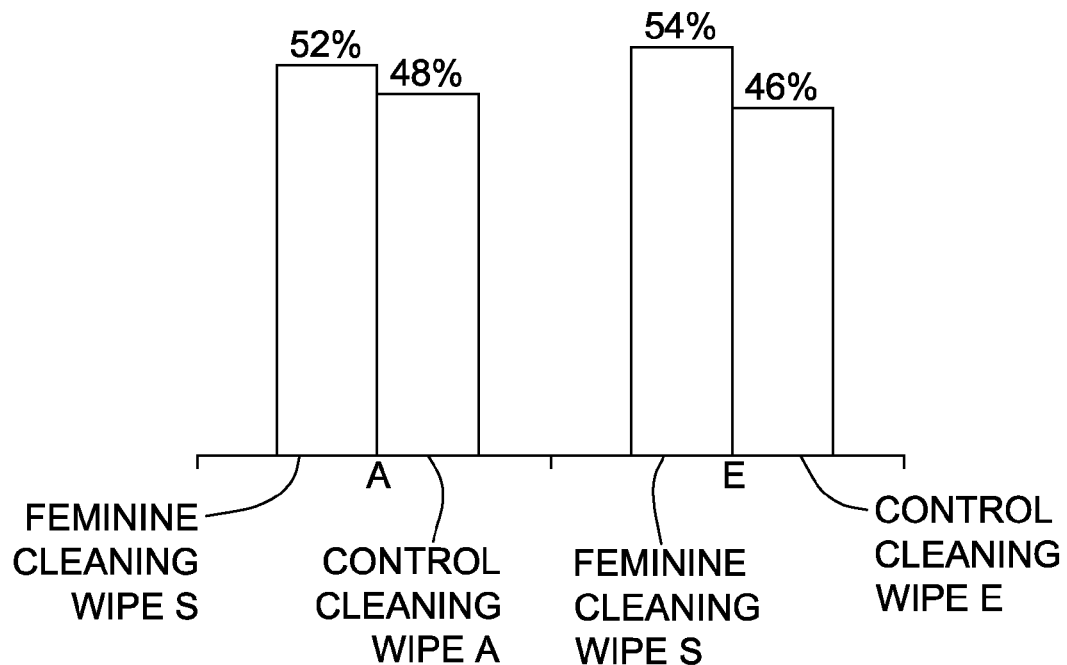
FIG. 1B is a graph comparing overall preference of a feminine cleaning wipe including a silicone amine and two commercially available feminine cleaning wipes as evaluated in Example 3.

As shown in FIG. 1A, feminine cleaning wipe S containing Silamine® PW13065 was preferred over control wipe N, which did not contain Silamine® PW13065, on attributes including cleanliness and afterfeel of the skin. Additionally, feminine wipe S was preferred overall when compared to commercial control wipes A and E (FIG. 1B).

This written description uses examples to disclose the invention, including the best mode, and also to enable any person skilled in the art to practice the present disclosure, including making and using any compositions or products and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A cleansing product comprising a substrate and a silicone reactive amino containing dimethicone copolyol having the formula:

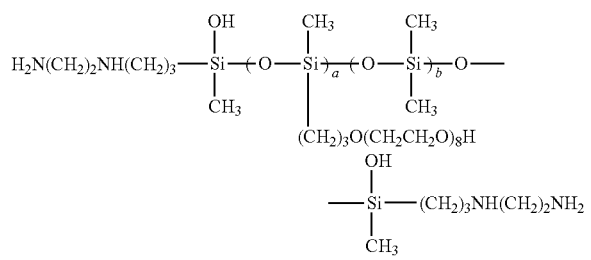

wherein a is an integer ranging from 5 to 500 and b is an integer ranging from 1 to 100.

2. The cleansing product of claim 1 wherein a is an integer ranging from 100 to 450.

3. The cleansing product of claim 2 wherein b is an integer ranging from 2 to 10.

4. The cleansing product of claim 1 comprising from about 0.05% by weight to about 50% by weight silicone reactive amino containing dimethicone copolyol.

5. The cleansing product of claim 1 comprising from about 0.01% by weight to about 25% by weight silicone reactive amino containing dimethicone copolyol.

6. The cleansing product of claim 1 wherein the substrate is a nonwoven substrate.

7. The cleansing product of claim 1 wherein the substrate is a woven substrate.

8. A wet wipe comprising a substrate and a wetting solution comprising a silicone reactive amino containing dimethicone copolyol having the formula:

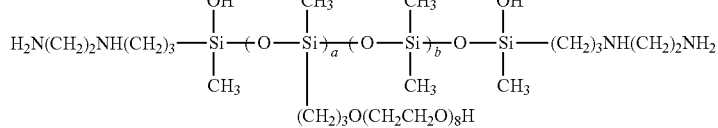

wherein a is an integer ranging from 5 to 500 and b is an integer ranging from 1 to 100.

9. The wet wipe of claim 8 wherein a is an integer ranging from 100 to 450.

10. The wet wipe of claim 9 wherein b is an integer ranging from 2 to 10.

11. The wet wipe of claim 8 wherein the wetting solution comprises from about 0.05% by weight to about 50% by weight silicone reactive amino containing dimethicone copolyol.

12. The wet wipe of claim 8 wherein the wetting solution comprises from about 0.01% by weight to about 25% by weight silicone reactive amino containing dimethicone copolyol.

13. The wet wipe of claim 8 wherein the wetting solution further comprises one or more electrolytes.

14. The wet wipe of claim 13 wherein the electrolyte is selected from the group consisting of sodium chloride, sodium bromide, potassium chloride, ammonium chloride, ammonium sulfate, zinc chloride, calcium chloride, magnesium chloride, magnesium sulfate, sodium nitrate, sodium methyl sulfate, and combinations thereof.

15. The wet wipe of claim 8 wherein the wetting solution further comprises a surfactant selected from the group consisting of nonionic surfactants, anionic surfactants, cationic surfactants, amphoteric surfactants, zwitterionic surfactants, and combinations thereof in an amount of from about 0.01% by weight to about 60% by weight surfactant.

16. The wet wipe of claim 8 wherein the wetting solution further comprises a skin benefit ingredient selected from the group consisting of emollients, surfactants, fragrances, preservatives, organic or inorganic acids, chelating agents, pH buffers, medicaments, antimicrobials, or combinations thereof.

17. The wet wipe of claim 8 wherein the substrate is a fibrous material having a strength of at least 300 g/in and a dispersibility of no more than 100 g/in.

18. A personal care composition for imparting a perceivable aesthetic feel to skin, the composition comprising a carrier and from about 0.01% by weight to about 99.9% by weight of a silicone reactive amino containing dimethicone copolyol having the formula:

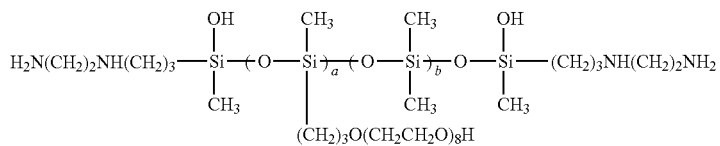

wherein a is an integer ranging from 5 to 500 and b is an integer ranging from 1 to 100.

19. The composition of claim 18 wherein a is an integer ranging from 100 to 450, and b is an integer ranging from 2 to 10.

20. The composition of claim 18 wherein the carrier is selected from the group consisting of water, glycol, lower chain alcohol, glycerin and glycerin derivatives, natural oils, synthetic oils, silicone derivatives, and combinations thereof.

21. The wet wipe of claim 8 wherein the wet wipe is a flushable moist wipe comprising a binder composition comprising a triggerable polymer.

* * * * *